United States Patent
Utterberg et al.

(10) Patent No.: US 6,383,158 B1
(45) Date of Patent: May 7, 2002

(54) DIALYSIS PRESSURE MONITORING WITH CLOT SUPPRESSION

(75) Inventors: David S. Utterberg, Seattle, WA (US); William J. Schnell, Libertyville, IL (US)

(73) Assignee: DSU Medical Corporation, Las Vegas, NV (US)

(*) Notice: Subject to any disclaimer, the term of this patent is extended or adjusted under 35 U.S.C. 154(b) by 0 days.

(21) Appl. No.: 09/203,274

(22) Filed: Dec. 1, 1998

(51) Int. Cl.[7] .......................... A61M 37/00; A61B 5/02; A61B 19/00; G01L 7/00
(52) U.S. Cl. ..................... 604/4.01; 604/6.16; 604/505; 604/156; 600/485; 128/898; 73/700; 210/741
(58) Field of Search ................ 128/898; 604/4–6, 604/6.1, 6.11, 6.16, 505, 67, 156, 131, 149; 422/82.13; 73/700, 706, 715; 600/485–488; 210/739, 741

(56) References Cited

U.S. PATENT DOCUMENTS

| | | | | |
|---|---|---|---|---|
| 3,581,733 A | * | 6/1971 | Grandjean ................ 128/2.05 |
| 3,863,504 A | * | 2/1975 | Borsanyi .................... 73/395 |
| 4,300,572 A | * | 11/1981 | Knighton ................... 128/674 |
| 4,431,009 A | * | 2/1984 | Marino, Jr. et al. ........ 128/673 |
| 4,444,198 A | * | 4/1984 | Petre ......................... 128/673 |
| 4,710,164 A | | 12/1987 | Levin et al. |
| 5,067,491 A | | 11/1991 | Taylor, II et al. |
| 5,148,811 A | * | 9/1992 | Messinger ................. 128/673 |
| 5,370,123 A | * | 12/1994 | Shinzato .................... 128/673 |
| 5,392,653 A | | 2/1995 | Zanger et al. |
| 5,454,374 A | | 10/1995 | Omachi ..................... 128/673 |
| 5,580,460 A | * | 12/1996 | Polaschegg ................ 210/646 |
| 5,693,008 A | * | 12/1997 | Brugger et al. ................ 604/4 |
| 5,823,967 A | * | 10/1998 | McArthur ................... 600/486 |
| 5,895,368 A | | 4/1999 | Utterberg ....................... 604/4 |
| 5,951,870 A | * | 9/1999 | Utterberg ................... 210/645 |

* cited by examiner

Primary Examiner—Angela D. Sykes
Assistant Examiner—Patricia Bianco
(74) Attorney, Agent, or Firm—George H. Gerstman; Seyfarth Shaw

(57) ABSTRACT

Pressure is sensed in blood flow tubing by placing an aqueous, preferably isotonic, substantially cell-free solution into branch connection tubing that connects in branching relation with the blood flow tubing at one end. The branch connection tubing also connects in use with a pressure transducer unit at its other end. An air volume is maintained, occupying a portion of the branch connection tubing which is adjacent to the other end. One flows positively or negatively pressurized blood through the blood flow tubing, with the result that the pressure of the blood is communicated through the aqueous solution and the air volume in the branch connection tubing to the pressure transducer unit, with the blood being spaced from the air volume. Preferably, substantially all of the branch connection tubing containing the aqueous solution and air volume has an inner diameter of substantially no more than 5 mm. This facilitates the continued separation of blood and solution when pressurized blood enters the branch connection tubing through the one end.

21 Claims, 4 Drawing Sheets

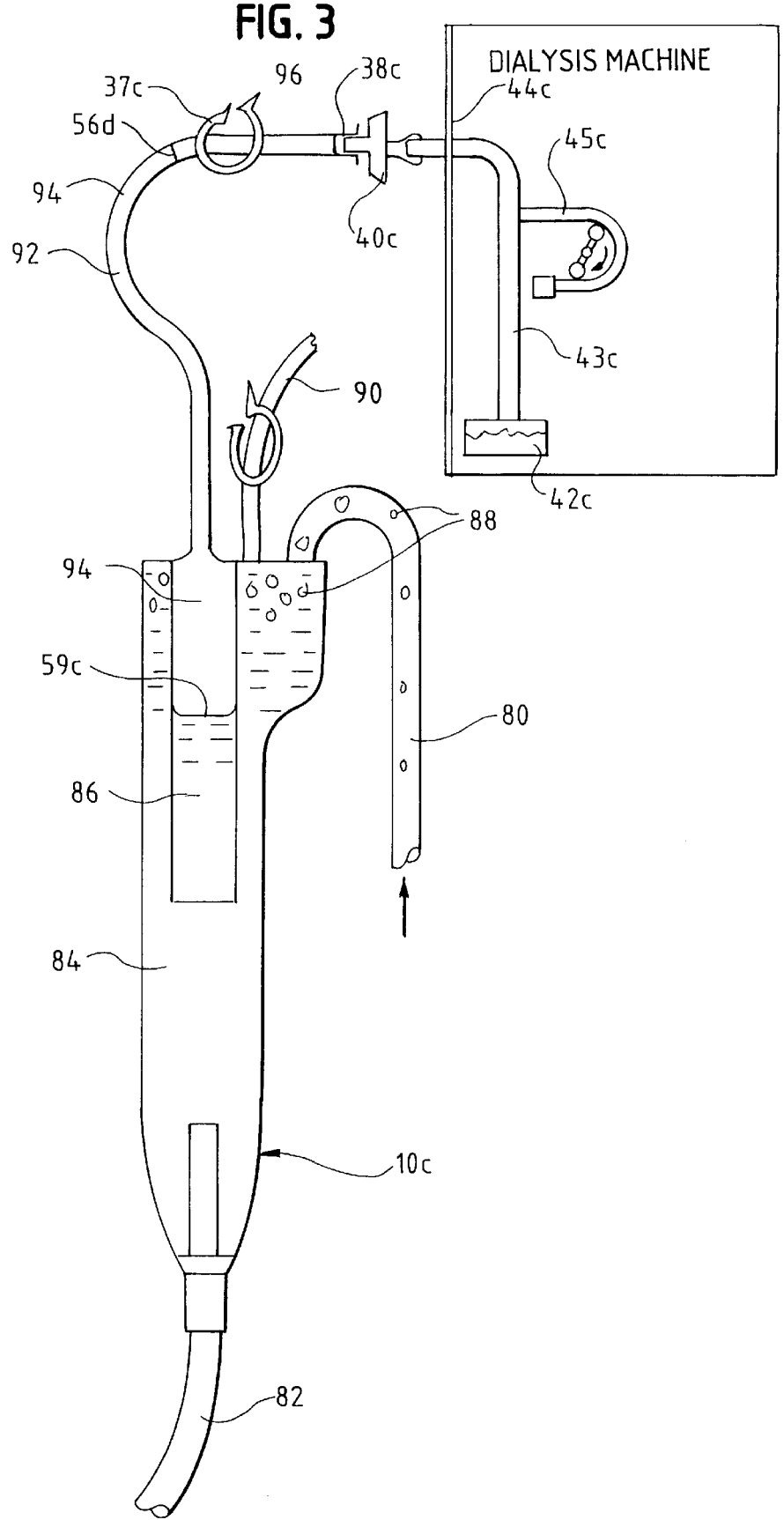

DIALYSIS PRESSURE MONITORING WITH CLOT SUPPRESSION

BACKGROUND OF THE INVENTION

Arterial and venous blood pressures in hemodialysis and other extracorporeal tube sets have traditionally been measured indirectly via a blood/air interface and air column communicating with a pressure measuring transducer. Such interface is typically located in an air trap chamber. The air column typically is contained within and communicates between various components: the top of a chamber, a pressure monitor tube (PMT), a dialysis machine tubing and a pressure measuring transducer housing within the dialysis machine. Also known are blood/air interfaces without a chamber where a PMT communicates with a blood tube at a "T" connection.

Each air column typically comprises a sterile chamber/PMT portion and an unsterile machine portion. A sterility barrier (or transducer protector), capable of transmitting air pressure while maintaining sterility, separates the sterile chamber/PMT portion from each unsterile machine portion. Typically the sterility barrier is a hydrophobic membrane permeable to air flow but not to aqueous liquids. Typically, the air column has a large cross section in the air trap chamber (10–35 mm ID) and a narrow cross section in the PMT (0.5–3.5 mm ID).

Such blood/air interfaces have numerous problems. First, blood exposed to air activates a clotting cascade usually in direct proportion to the blood/air interface surface area and to the degree of stagnation of the blood at the interface. Anticoagulants such as heparin are required to counteract such clotting tendency. Anticoagulants are costly and have numerous side effects for the patient.

Second, air in conventional air trap chambers can escape and enter the patient, even if no air enters the chamber in the incoming blood flow. That is, if and when the blood/air interface falls below the blood inlet (e.g., a downspout) the incoming blood flow causes cavitation at the interface and entrains air emboli in the downward blood flow, such that the air may escape the air trap chamber.

Third, air trap chambers often comprise over 20 percent of the size, weight and cost of the entire blood tubing set.

The fourth problem relates to blood/air interface level changes in the chamber due to pressure reductions (where liquid level goes down) and pressure increases (where liquid level goes up). Such level changes promote a risk of inhibiting accurate pressure measurements and may promote air emboli passing to the patient. The degree of blood/air interface level change is in direct proportion to the total volume of air in both the tube set and pressure machine portions according to Boyle's law. Machine air volumes typically vary from 2 cc to more than 10 cc, depending on manufacturer and model. PMT air volumes typically range from 0.5 cc to 6 cc. Chamber air volumes depend on the blood level chosen by the clinician, but typically range from 3 cc to 20 cc. With the blood pump off, blood pressures are zero, and the arterial and venous blood/air interfaces are at the level in the chamber initially chosen by the clinician. But when blood flows increase to typical speeds (e.g. 450 ml/min with 15G AVF needles), pre-pump pressures drop as much as −300 mmHg or more and post-pump pressures increase as much as +500 mmHg.

In the positive pressure case, the air volume may be compressed as much as 40 percent or more ((1160 mmHg−760 mmHg)/760 mmHg). If the chamber/PMT air volume is less than 40 percent of the total air volume, the blood/air interface level can rise into the PMT until it is stopped by the transducer protector. Blood is thus trapped in the transducer protector and typically clots, and the machine transducer is no longer able to accurately measure pressure. This is a highly dangerous situation. In the negative pressure case, the air volume may be expanded as much as 65 percent or more (760 mmHg/(760 mmHg−300 mmHg)). If the chamber blood volume is less than the expansion air volume, the blood/air interface may fall until it empties the chamber and passes air to the patient, causing air emboli, an even more dangerous situation.

A fifth problem relates to dialysis tube sets and dialyzers requiring priming with physiologic fluid to eliminate unwanted air prior to processing blood through the circuit. In typical prior art chambers, an initial saline prime creates a saline/air interface in an upper portion of the chamber at a position chosen by the physician. When blood flow starts, however, saline is completely displaced by blood due to the excellent mixing in these chambers. Typically, the blood inlet is close to the saline/air interface or points at the saline/air interface. Thus, the saline/air interface quickly becomes a blood/air interface.

Other prior art chambers have long blood inlet downspouts or other arrangements to enter the chamber well below the fluid level in the chamber and pointed away from the fluid level. For example, Fresenius AG has an air trap chamber designed to promote a blood/saline or plasma/air interface with the blood inlet directed transversely and located well below the interface of the chamber. In these chambers, the initial saline/air interface may be set well above the blood inlet to the chamber. Blood is slightly heavier than saline (the cellular elements more so than plasma), so when blood enters the chamber (especially at low or moderate flow common in Europe and Japan), blood tends not to invade the stagnant (saline) area above the inlet level. This is often sufficient to stratify into a blood/saline/air interface or even stratify into a blood/plasma/air interface since plasma is almost the density of saline and will rise above blood's cellular elements if relatively undisturbed. As saline-to-air contact initiates no clotting-cascade, and plasma-to-air contact has few if any initiators for clotting, this design is thought to provide clotting protection over a normal blood/air interface.

In practice, however, this approach has had little practical value. Dialysis has many events that cause abrupt pressure changes: peristaltic pump action at high flows (a large pressure pulse where flow instantaneously slows, stops or even reverses with each roller stroke); pump stoppages due to alarms; patient movements, patient coughing, line kinking, inadvertent clamping, etc. These pressure changes cause the fluid level to rise or fall rapidly. In those chambers which have large cross sectional areas, "plug flow" does not occur. Instead, blood "burps" up into the stagnant plasma or saline layers, and displaces some or all of the plasma and/or saline. Now blood is in a stagnant area of the chamber with a blood/air interface, and significant clotting is created. "Plug flow" is the movement of two fluids in a tube as separate but intact bodies, such that an interface separating the two fluids is maintained. Plug flow is easier with relatively small ID tubes than larger tubes.

Sixth, a greater destroyer of a stable blood/plasma or saline interface in air trap chambers is air bubbles entrained in the incoming blood flow. These bubbles rise to the surface, passing through any saline or plasma layers because the cross sectional area of these chambers is much larger than the diameter of these bubbles. If bubbles enter a tube small enough that the bubble bridges from wall to wall, frictional forces stop the bubble from rising further, unless convective forces push on the fluid column. The bubble locks the fluid above the bubble from mixing with the fluid below the bubble (as artfully employed by clinical analyzers). Bubbles of less diameter than the tube they are carried in, however, will freely rise. Due to the non-airfoil shape of these bubbles, they drag up blood in their wake into the plasma/saline layers. It takes relatively few bubbles to completely displace essentially all plasma or saline with blood creating a stagnant blood/air interface. As above, this blood is now subject to the stagnation clotting cascade mechanism.

The prior art also includes Cobe machines that mate with a sterile cassette tube set with a non-porous, diaphragmatic sterility barrier mounted directly in an air trap chamber side wall, which eliminates the need for a pressure monitor tube. This set does, however, comprise a blood/air interface in the air trap chamber. Brugger et al U.S. Pat. No. 5,693,008 shows an arrangement of machine and tube set which eliminates the blood/air interface. Zanger U.S. Pat. No. 5,392,653 discloses blood pressure measurement without an blood/air interface, using a diaphragm in direct connection with a force transducer.

Another prior art of a Japanese company seeks to overcome the blood/air problem by interposing a low weight fat between the blood and air phases. It discloses injecting a low weight fat into each chamber. Because this fat's density is significantly below that of blood or plasma, it floats on top and prevent a blood/air interface, and if the layer is disrupted by bubbles or pressure pulses, the fat again rises to become the air interface. It also claims that fat does not initiate any clotting cascade mechanism. The expense and pharmaceutical regulatory approval required of this approach has apparently prevented its use.

Worldwide, all hemodialysis machines in use today are designed for blood/air interface tube sets. These machines provide over 120 million dialyses per year for over 800,000 end stage renal disease patients. Recent disclosures of airless blood tubing sets will require new machines and many years to bring their benefits to a substantial number of patients. It is an objective of this invention to create tube sets and methods for all presently existing machines, and new machines, that eliminate the blood/air interface. It is also a preferred objective of this invention to reduce the amount of anticoagulant required to perform dialysis. It is a preferred objective of this invention to reduce clotting in the tube sets, putting the saline column at least partially in a tube that has an inner diameter that substantially promotes "plug flow" and keeps the saline in between the blood phase and the air phase. It is a preferred objective of this invention that no modification of the existing machines is required to use these tube sets and methods. Also by this invention, the number of tube set components can be reduced in number, size and cost.

DESCRIPTION OF THE INVENTION

By this invention, the blood/air interface can be eliminated while sensing pressure in blood flow tubing. The method comprises: placing an aqueous, typically physiological, isotonic, substantially cell-free solution, (typically normal medical saline solution or the like) into branch connection tubing that connects in branching relation with the blood flow tubing at one end, and connecting with a pressure transducer unit at its other end. An air volume is maintained to occupy a portion of the branch connection tubing which is adjacent to the other end near the pressure transducer unit. One then flows positively or negatively pressurized blood through the blood flow tubing. Thus, the pressure of the blood is communicated through the aqueous solution and then the air volume in the branch connection tubing to the pressure transducer unit, with the blood being spaced from the air volume.

Typically, substantially all of the branch connection tubing containing the aqueous solution and air volume has an inner diameter of substantially no more than 5 mm. One purpose of this is to facilitate continued separation of blood and the solution described above, when pressurized blood enters the branch connection tubing through the one end. Preferably, the inner diameter of the tubing will be substantially no more than 3.5 mm.

While the above facilitates the continued separation of blood and solution, a certain amount of mixing may take place in the branch connection tubing so that the aqueous, cell-free solution can become pink in the area adjacent to the blood-solution interface. For this and other reasons, it is preferred for a priming solution tube, which is connected to a source of priming solution, to be connected in branching relation with the branch connection tube. Thus, added portions of priming solution can be periodically added to push downwardly the aqueous solution in the branch connection tubing, which has become mixed with a small amount of blood, into the blood flow tubing during operation, so that the aqueous solution in the branch connection tubing can remain substantially blood cell-free.

In this invention, the blood/air interface of the prior art is thus replaced on a continuing basis by a blood/saline/air interface. A saline column (or other appropriate solution) is interposed during the priming procedure between the blood phase and the air phase. The saline column, saline/air interface and air column are located within the branch connection tubing communicating with a main blood flow tube, optionally with an enlarged chamber of the main blood flow tube. Preferably, such a blood chamber is filled completely (eliminating any blood/air interface), and is well mixed. Preferably, the branch connection tubing is sized to promote plug flow (so as to prevent the blood/saline interface from rapidly degrading with pressure pulses, alarms, patient movements and changes in blood pressure from atmospheric to operating pressures) and to resist free flow of air bubbles. Its inlet to the blood flow tubing may be positioned below the highest point in the chamber so as to resist entry of air bubbles.

The ratio of the saline volume in the chamber/PMT to the air volume in the system is sufficient to prevent transducer protectors of the pressure transducer unit from being wetted out in a positive pressure situation, or air being dumped into the main blood tube in a negative pressure situation. An in-line chamber may be added to the branch connection tubing to help accomplish this.

This invention may use a variety of designs and methods, with and without air trap chambers in the blood tubing or in branch saline or air tubing.

The aqueous solution may be formulated to be compatible with blood to suppress clotting, for example, by the addition of heparin or the like. The heparin line which is conventionally found in extracorporeal blood sets may be connected in another branching connection to the branch connection tubing, typically at a connection downstream of a branch connection with the source of added aqueous solution, for priming and patient fluid maintenance.

The branch connection tubing may, if desired, define an in-line chamber that preferably extends for no more than 10 percent (and typically less than 7 percent) of the length of the branch connection tubing. The purpose of this is to provide an increased volume to the branch connection tubing, to reduce the movement of particularly the interface between blood and the aqueous solution as blood pressure changes.

Also, it may be desirable for the branch connection tubing to comprise a flow-resisting constriction to slow movement of the interface boundary between the blood and aqueous solution upon pressure changes. Particularly, the flow-resisting constriction is preferably positioned at a portion of the branch connection tubing that carries the aqueous solution, farther up the tubing than blood would be expected to travel. Thus, the movement of the interface boundary between the blood and the aqueous solution may be slowed in a manner to reduce mixing of blood and solution at their interface in the event of large, sudden pressure changes. Preferably, the flow-resisting constriction is positioned at a portion of the branch connection tubing that carries the aqueous solution, to spare the blood from the stresses that might be encountered by passing through such restriction.

In another embodiment, the main blood flow tubing may comprise an enlarged chamber portion. The branch connection tube connects in branching relation with the blood flow tubing through a wall of the enlarged chamber portion. The enlarged chamber portion is preferably completely filled with aqueous solution at the end of priming of the set for use, and then it becomes completely filled with blood, except for air bubbles that may be trapped in the chamber during the use, and are periodically drawn away by a syringe through an injection site or branch tube, or through a hydrophobic vent, in conventional manner.

In this embodiment, the branch connection tube may have a proximal end portion which extends for a substantial distance into the enlarged chamber portion inwardly through its wall. In use, the interface boundary between the blood and aqueous fluid may occupy the proximal end portion.

The branch connection tube may be integral and nonseparable along its length from its connection to the main blood flow tubing, to the connector at its other end through which it connects with the pressure transducer unit. Alternatively, the branch connection tube may be separable into two or more serial components by means of a pair or pairs of engaging connectors in various ways as may be desired. For example, the branch connection tube may be separable by a pair of adjoining connectors positioned between a T- or Y-junction where a line to a source of priming solution connects with the branching tubing, and to the main blood tube, so that most of the branch connection tubing and its connected priming solution tube can be a separate set. Alternatively, the tube that connects between the priming solution and the branch connection tubing may be a separate set, while the branch connection tubing is integral with the main blood tube. As another alternative, the branch connection tubing may carry an in-line chamber comprising preferably less than ten percent of the length of the branch connection tubing, and the line connected to the source of aqueous, cell-free solution (priming solution) can connect to that chamber in a form of a branch connection.

Branch connection tubings may connect to the blood tube both upstream (negative pressure) and downstream (positive pressure) of roller pump tubing, or other tubing which engages another type of pump for pumping through the tubing. Each of these branch connection tubings may communicate with a pressure transducer so that upstream and/or downstream pressure from the pump can be measured. The tubings will each have an air filled section adjacent the transducer protector and an aqueous solution-filled section adjacent the blood tube in accordance with this invention. Also, if desired, tubing may connect to each of these tubings in branching connection to provide access to a source of aqueous, isotonic, substantially cell-free solution (such as normal saline solution) so that such solution may be applied to the branch connection tubing. This solution may also be added back to the blood after treatment by hemofiltration for example, to give the patient a desired hematocrit in the blood before returning the blood to the patient.

The invention of this application may be utilized in the particular sets and the process of automatic priming thereof that fall under the scope of the invention as described in Utterberg U.S. patent application Ser. No. 08/954,804, filed Oct. 21, 1997, entitled "Automatic Priming of Blood Sets" now U.S. Pat. No. 5,951,870.

DESCRIPTION OF THE DRAWINGS

FIG. 3 is an elevational view of a portion of a third hemodialysis blood circuit, showing another embodiment of this invention.

DESCRIPTION OF SPECIFIC EMBODIMENTS

Figure 1:
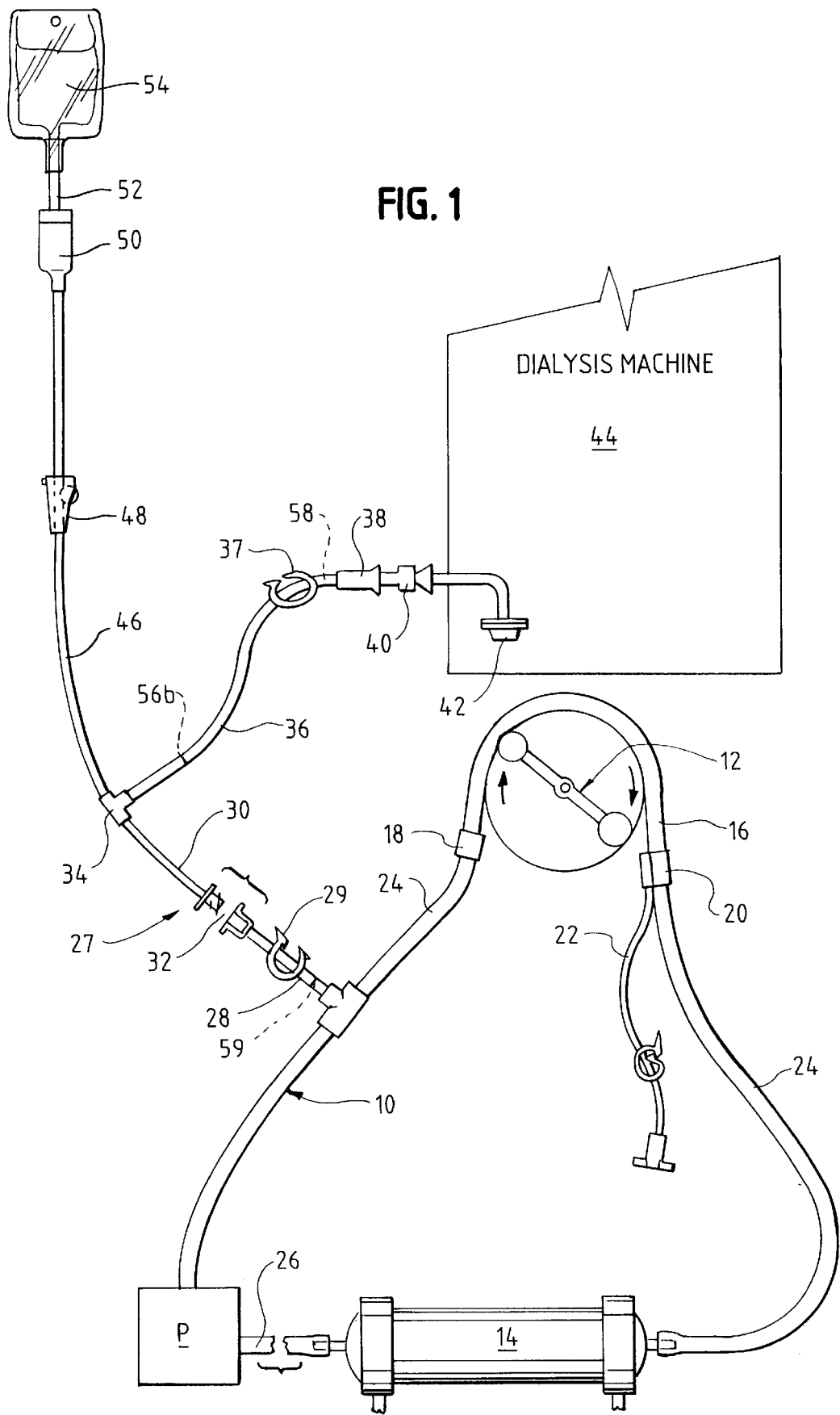
FIG. 1 is a partially schematic view of a hemodialysis blood circuit system, showing one embodiment of the invention.

Referring to the drawings, FIG. 1 shows an embodiment of the invention for arterial pre-pump pressure monitoring, showing a partially schematic blood flow circuit for removing blood from patient P, passing the blood through blood flow tubing system 10 including arterial line 24, and a generally conventional blood pumping system 12, passing blood through a hemodialyzer 14 or other blood processing device such as a hemofiltration device, and then via venous line 26 returning the blood to the patient. As is conventional, blood pump 12 may comprise a length of peristaltic pump tubing 16 having connectors 18, 20 at the respective ends thereof, which may connect with branch connection line or lines 22 in conventional manner. Branch connection line 22 may be used to add heparin, to remove blood samples, or the like.

As shown in FIG. 1, a section 28 of branch connection tubing 27 is provided, being integral with arterial blood tubing 24, and connecting with a second section 30 of the branch connection tubing 27 by means of a conventional luer lock connector system 32 or the like. Branch connection tubing section 30 defines a flow path that extends through T-connector 34 and then through a third section 36 of branch connection tubing 27 that terminates in a female luer connector 38.

Connector 38 is shown to connect to a transducer protector 40 of known design, which carries an air permeable, liquid blocking barrier, to protect a conventional pressure transducer 42, which is positioned within the housing of a conventional dialysis machine 44 of present commercial design, which machine controls the flow and dialysis conditions through the system and monitors necessary parameters in known manner. Usually, dialyzer 14 is carried on the dialysis machine 44, although not so shown in this schematic view of FIG. 1.

T-connector 34 has a third connection which communicates with priming solution tube 46, which carries a roller clamp 48, and terminates at its upper end in a conventional I.V. drip chamber 50. Drip chamber 50 has a conventional spike 52, which is shown to be in connection with a bag of medical saline solution 54.

Figure 1A:
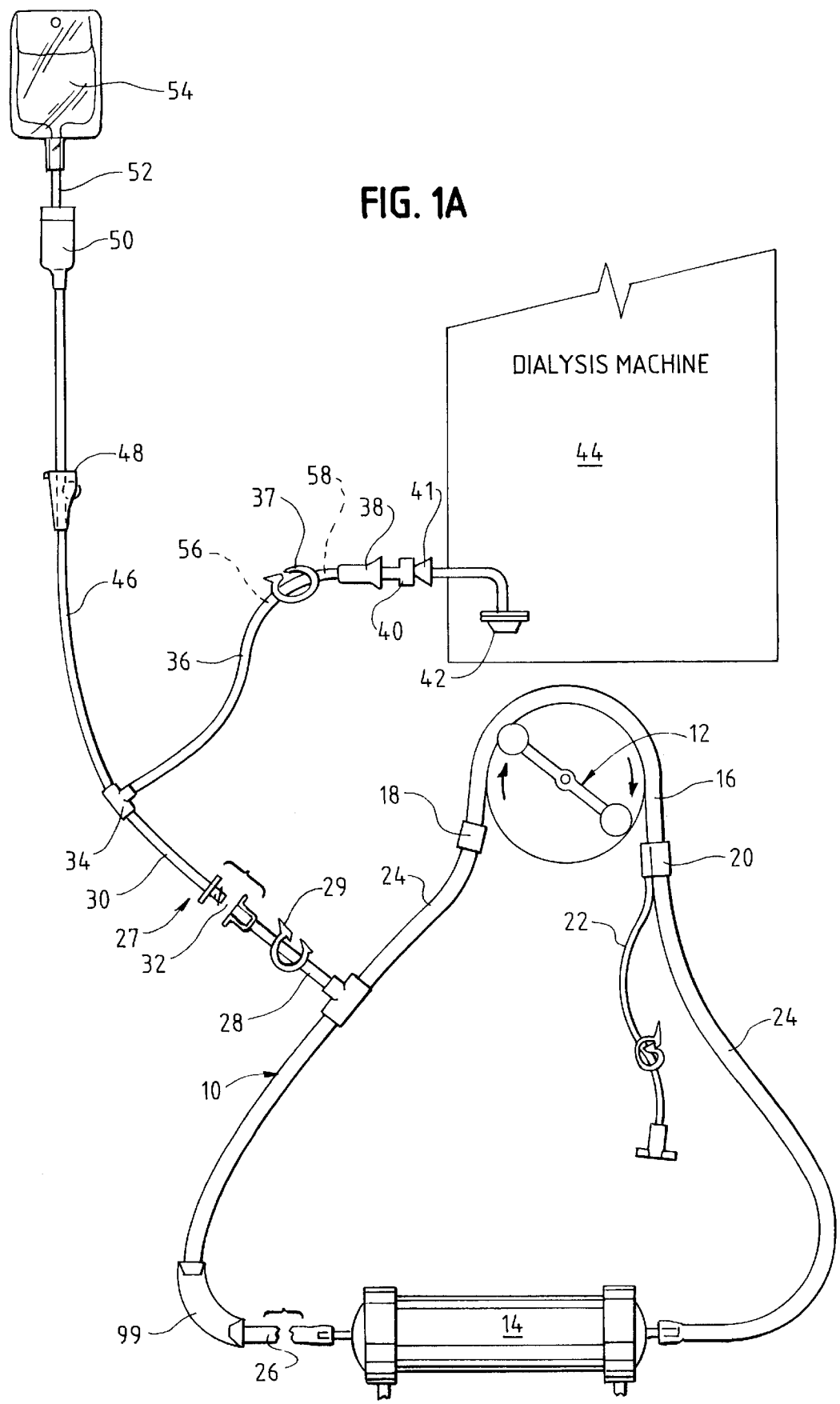
FIG. 1A shows the circuit system of FIG. 1 in its priming mode prior to adding blood.

In accordance with this invention, referring to FIG. 1a, flow of liquid from saline bag 54 is opened after all connections are made so that saline solution fills the sections of branch connection tubing 27, and also flows into arterial blood flow tubing 24 to prime the respective arterial and venous tubing sets 24, 26 and the dialyzer 14, preferably via removable recirculation tube 99 prior to patient connection. Clamp 37 may be opened so that an amount of the solution from bag 54 passes into tube section 36 by venting out via temporarily unconnected transducer protector 40, stopping at some clinically chosen point along the tube such as point 56, where a solution-air interface is formed after transducer protector 40 is sealed to the machine fitment 41. This interface is formed because there is no venting outlet for tube 36 on its end connected with transducer protector 40 and pressure transducer 42.

Then, referring again to FIG. 1, roller clamp 48 may be typically closed, patient P is connected, and roller pump 12 begins operation, drawing blood from patient P into arterial set 24, while returning first priming solution and then blood to the patient via dialyzer 14 and then venous set 26 in a conventional dialysis circuit.

Clamps 29 and 37 remain open, so that negative pressure in the blood flow tubing system 10 upstream of pump 12 is directly transmitted through the branch connection tubing sections 28, 30, 36 to the pressure transducer 42. This negative pressure can be read out and displayed through the electronics of dialysis machine 44, and automatic shut off can occur when wrong pressures are sensed.

As this negative pressure is monitored during the operation of roller pump 12 and the flow of blood through tubing system 10, dynamic pressure pulse variations may take place, and will be transmitted through tubing sections 28, 30, 36 to the pressure transducer 42, for a moment-by-moment readout of the pressure. As negative pressure increases, the saline/air interface 56 may move down line 36 to position 56b in a "plug flow" type manner, forming a stable solution-air interface because there is little mixing between the priming solution in tubing 36 and the blood. This happens because branch connection tubing sections 28, 30, 36 each have an inner diameter of no more than about 5 mm., and typically less than 3.5 mm. The solution-air interface 56b will correspondingly move back and forth, and the air found in section 58 of tubing 36 will be relatively compressed and decompressed as the pressure in the system fluctuates, transferring the moment-by-moment pressures to pressure transducer 42.

Branch connection tubing sections 28, 30, 36 can be of a sufficient length that the pressure fluctuations encountered fail to drive the liquid-air interface 56 into transducer protector 40 at maximum pressures encountered, while also preventing minimum pressures from causing liquid-air interface 56b to be driven down tubing sections 28, 30 to cause air to enter blood flow tubing 10.

During operation, it may be desirable to open roller clamp 48 to allow more normal saline priming solution to pass into the branch connection tubing 27, and particularly tubing sections 28, 30, if blood begins to mix with the cell-free aqueous solution in sections 28, 30. The solution which has become pink due to admixing with blood can pass into blood flow tubing circuit 10, so that a discrete blood-solution interface 59 can be easily recreated as needed. The pressure head of solution from the elevated bag 54 is generally sufficient to drive solution into the blood circuit 10. Thus, stagnant blood residing in the branch tubing 27, and obscuring the blood-solution interface 59 by mixing with the solution, can be returned to the main circuit 10. The effect of this is to suppress clotting, as well as to maintain a clear blood-solution interface 59, since stagnant blood can be returned to the circuit 10 before the clotting process gets under way. This interface 59 also can move along branch connector tubing 27, 28 with varying pressures.

Figure 2:
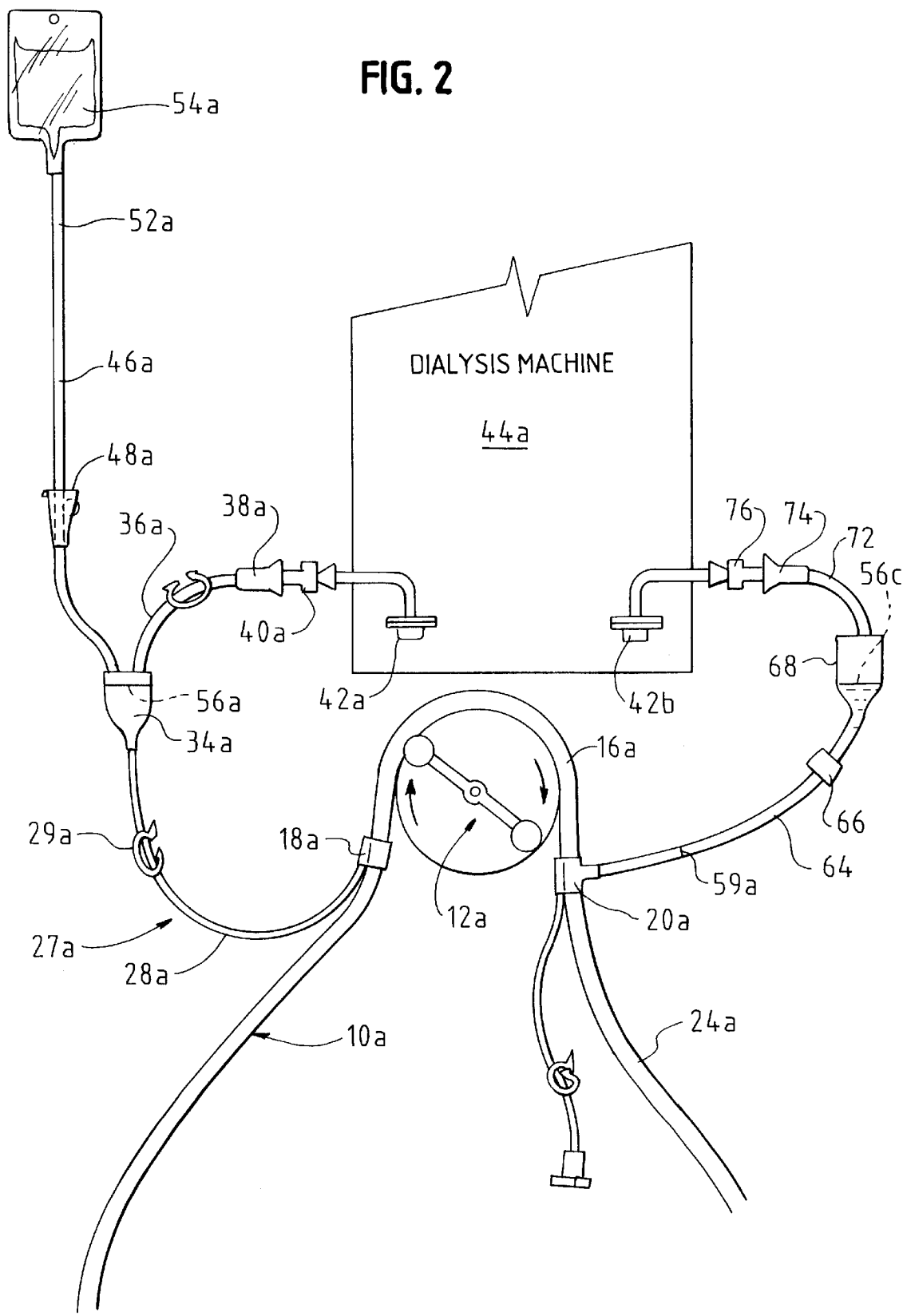
FIG. 2 is an elevational view of a portion of another hemodialysis blood circuit showing other embodiments of the invention of this application.

Referring to FIG. 2, a similar dialysis blood flow circuit 10a is shown, with a similar branch connector tube 27a for pre-pump arterial negative pressure measurement, the system having components of similar number to the reference numerals of FIG. 1, but with the added suffix "a." Branch connector tubing 28a represents an integral combination with the other sections of the branch connection tubing 27a, extending from a connector 18a at one end of roller pump tubing 16a to female luer 38a connecting with transducer protector 40a and transducer 42a in dialysis machine 44a. The integral connection of tubing 28a to the main blood flow tubing 10a may be made at connector 18a in conventional manner.

As a further modification, a chamber 34a is substituted for the previous T-connector of similar number, which chamber provides the function of a T-connector with respect to priming solution tube 46a, which can connect through spike 52a to a saline bag 54a. In this embodiment, chamber 34a can comprise the typical site of the liquid-air interface 56a, being placed in the enlarged diameter chamber 34a relative to the tubing 28a, 36a. This also eliminates the need for chamber 50 of the previous embodiment, since chamber 34a can serve both as a drip chamber and as an enlarged chamber to hold the priming solution-air interface 56a. Thus, as the system is negatively pressurized with roller clamp 48a closed, a larger internal volume is provided to the branch connection tubing system 27a, so that the corresponding movement of priming solution-air interface 56a is low because of the enlarged volume of chamber 34a. At maximum negative pressures, preferably solution-air interface 56a stays within chamber 34a. Thus, there is greatly reduced risk of the priming solution air interface 56a moving down tube 28a to drop into blood flow tubing system 10a.

As before, blood in line 28a can be eliminated if needed, being returned to the main blood flow circuit 10a by the addition of a small amount of added solution from saline bag 54a by control of roller clamp 48a. Thus a clear blood-solution interface can be maintained, at times within connector 18a, and clotting can be suppressed.

The downstream connector 20a, which connects the larger diameter of roller pump tubing 16a with a section of arterial tubing 24a, has a second branch connection line 64, for post pump arterial positive pressure measurement, in accordance with this invention. By this invention, branch connection line 64 may be at least partially filled with saline solution during the priming step to a solution-air interface level 56c, so that, during blood processing, at maximum positive pressures, solution/air interface 56c may be provided in chamber line 68, the position of interface 56c moving back and forth in a manner dependent upon the pressure in the system.

The blood/solution interface 59a will move also with pressure from adjacent to connector 20a up the line 64 in the same manner, dependent upon the positive pressure in the system.

A constricted flow resistor 66 may be provided to slow the movement of interface 59a with pressure changes, so that mixing of blood and solution is suppressed.

Branch line 64 connects to an enlarged chamber 68, where the liquid-air level or interface 56c is provided. The branch line system then continues with a top line 72, extending from the top of chamber 68 and terminating in a luer connector 74, which releasably connects with transducer protector 76, of a design similar to transducer protectors 40 and 40a. Pressure transducer 42b then connectg in sealed manner to line 72 through the transducer protector 76, so that pressure in the system is transmitted to pressure transducer 42b through branch line 64, chamber 68, and top line 72, in a manner similar to the functioning of the previous transducers 42 and 42a. A priming drain line can optionally be added, typically connecting to the top of chamber 68, to facilitate priming of the blood set 10a and the entire system in a manner as described in the previously cited Utterberg U.S. Pat. No. 5,951,870.

Thus, the pressure of the system can be monitored from two different positions, one negative pressure upstream of the pumping site 12a and one positive pressure downstream of the same pumping site.

FIG. 3 shows a modification of the pressure sensing system of this invention. Typically, this is a modification of the positive pressure measurement system, preferably on the venous or return line to the patient where air trapping is required to prevent air emboli from reaching the patient. FIG. 3 shows a positive pressure embodiment.

Blood flow chamber 10c connects with flow tubing 80, 82, which may be part of either an arterial or a venous set portion of a blood flow circuit for a hemodialyzer system, a hemofiltration system, a plasmapheresis system or the like.

Chamber 84 looks like a conventional air removal chamber for a conventional hemodialysis set, but operates in a different manner. Particularly, chamber 84 is substantially completely filled with liquid, and not having the conventional liquid level with an air space above it. Rather, the chamber is completely filled first with priming solution, which is then replaced with blood. Incoming entrained air bubbles 99 within inlet tube 90 collect near the top of the chamber, and may be withdrawn as desired through tube 90 or through a hydrophobic vent when an air space does form.

Preferably, chamber 84 includes depending tube 86 (which descends at least partially into chamber 10c) and communicates, with branch connection tubing 92 at the top of chamber 84. Alternately branch tubing 92 may contain a chamber and/or a restriction similar in concept and function to related items 68 and 66 of FIG. 2. Branch connection tubing 92 connects with a female luer connector 38c in a manner similar to previous embodiments, and female luer connector 38c removably connects with transducer protector 40c. Transducer system 42c, of known design, is typically positioned within dialysis machine 44c as in previous embodiments to sense pressures in line 92 through connection line 43c. Clamp 37c can be closed except when pressure is being genged or saline solution level adjusted. Chamber level adjust line and pump 45c is conventionally provided here and in the other pressure sensor systems shown.

Such a positive pressure system, upon priming, will have a saline/air interface initially set at a point within depending tube 86 (if present) or in tube 92 (or chamber if present). With the addition of blood at operating flows and pressures, the saline/air interface will move upward, causing a blood/saline interface to be formed within the branching line system (of which depending tube 86 may be a part, if present). For example, at operating pressure a salina/blood interface may be formed at 59c. Changes of pressure may cause relatively little movement of interface 59c if the diameter of depending tube 86, if present, is relatively larger. Such enlarged diameter can cause the continuous tychanga of blood to and from the interior of depending tube 86 without serious disruption of the blood/solution interface.

A saline/air interface 56d can be provided in line 92, so that the saline never reaches transducer protector 40c under normal circumstances. Thus, the pressure is sensed by transducer 42c on a moment-by-moment basis, being transmitted from the blood through the saline solution 94, and then the air 96, each found in a separate section of tubing 92, so that the air in transducer tube 43c is compressed and the pressure is sensed by transducer 42c. Thus, the dialysis system 44c may exhibit pressure readouts, and may undergo emergency shutoff in the event of a large pressure fluctuation.

If desired, a collapsible pillow that optionally is completely filled with solution may provided to any of the branch lines of any of the disclosed embodiments, in addition to or as a substitute for chambers 34a or 68, for example. The solution-air interfaces 56a, c can optionally be located elsewhere.

The above has been offered for illustrative purposes only, and is not intended to limit the scope of the invention of this application, which is as defined in the claims below.

That which is claimed:

1. The method of sensing pressure in extracorporeal blood flow tubing, which comprises: placing an aqueous, isotonic, substantially cell-free solution into branch connection tubing that connects in branching relation with said blood flow tubing at one end, and connecting with a pressure transducer unit at its other end, while maintaining an air volume occupying a portion of said branch connection tubing adjacent to said other end; and flowing positively or negatively pressurized blood through said blood flow tubing, whereby the pressure of said blood is communicated through said aqueous solution and the air volume in said branch connection tubing to said pressure transducer unit with the blood being spaced from the air volume.

2. The method of claim 1 in which said aqueous solution is formulated to be compatible with blood to suppress clotting.

3. The method of claim 1 in which substantially all of the branch connection tubing containing said aqueous solution and air volume has an inner diameter of substantially no more than 5 mm., to facilitate continued separation of blood and said solution when pressurized blood enters said branch connection tubing through said one end.

4. The method of claim 3 in which portions of said branch connection tubing which have an inner diameter of no more than 5 mm. respectively contain blood, said aqueous solution, and air in substantially separate portions while pressure of the blood is being continuously sensed.

5. The method of claim 3 in which said branch connection tubing defines an in-line, enlarged chamber that extends for no more than ten percent of the length of said branch connection tubing.

6. The method of claim 1 in which said branch connection tubing comprises a flow-resisting constriction to slow movement of an interface boundary between blood and said aqueous solution in said branch connection tubing upon pressure changes.

7. The method of claim 6 in which said flow-resisting constriction is positioned at a portion of said branch connection tubing that carries said aqueous solution.

8. The method of sensing pressure in extracorporeal blood flow tubing, which comprises: placing an aqueous, isotonic, substantially cell-free solution into branch connection tubing that connects in branching relation with said blood flow tubing at one end and connects with a pressure transducer unit at its other end, while maintaining an air volume occupying a portion of said branch connection tubing adjacent to said other end; and flowing positively or negatively pressurized blood through said blood flow tubing, whereby the pressure of said blood is communicated through said aqueous solution and the air volume in said branch connection tubing to said pressure transducer unit with the blood being spaced from the air volume, and periodically providing more aqueous, isotonic, substantially cell-free solution through a priming solution tube connected to a source of priming solution and connecting in branching relation with said branch connection tube, to flush said aqueous solution in said branch connection tubing which has become admixed with blood into the blood flow tubing.

9. The method of claim 8 in which substantially all of the branch connection tubing containing said aqueous solution and air volume has an inner diameter of substantially no more than 5 mm., to facilitate continued separation of blood and said solution when pressurized blood enters said branch connection tubing through said one end.

10. The method of claim 8 in which the majority of said branch connection tubing has an inner diameter of substantially no more than 5 mm.

11. The method of sensing pressure in extracorporeal blood flow tubing, which comprises: placing an aqueous, isotonic, substantially cell-free solution into branch connection tubing that connects in branching relationship with said blood flow tubing at one end, and connecting with a pressure transducer unit at its other end, while maintaining an air volume occupying a portion of said branch connection tubing adjacent to said other end, in which substantially all of the branch connection tubing containing said aqueous solution and air volume has an inner diameter of substantially no more than 5 mm, and in which portions of said branch tubing which have an inner diameter of no more than 5 mm respectively contain blood, said aqueous solution, and air in substantially separate portions; and flowing positively or negatively pressurized blood through said blood flow tubing, whereby the pressure of said blood is communicated through said aqueous solution and the air volume in said branch connection tubing to said pressure transducer unit with the blood being spaced from the air volume by said aqueous solution and pressure of the blood is being continuously sensed, and further wherein said blood and aqueous solution move longitudinally in said tubing of no more than five millimeters diameter as said pressure varies.

12. The method of claim 11 in which said branch connection tubing defines an in-line, enlarged chamber that extends for no more than 10 percent of the length of said branch connection tubing.

13. The method of sensing pressure in extracorporeal blood flow tubing, which comprises: placing an aqueous, isotonic, substantially cell-free solution into branch connection tubing that connects in branching relation with said blood flow tubing at one end and connects with a pressure transducer unit at its other end, while maintaining an air volume occupying a portion of said branch connection tubing adjacent to said other end; and flowing positively or negatively pressurized blood through said blood flow tubing, whereby the pressure of said blood is communicated through said aqueous solution and said air volume in said branch connection tubing to said pressure transducer unit, with the blood being spaced from the air volume by the aqueous solution, in which substantially all of the branch connection tubing containing said aqueous solution and air volume has an inner diameter of substantially no more than 5 mm. to facilitate continued separation of blood and said solution, when pressurized blood enters said branch connection tubing through said one end, and in which portions of said branch connection tubing which have an inner diameter of no more than 5 mm respectively contain blood, said aqueous solution, and air in substantially separate portions, while pressure of the blood is being continuously sensed, and further including the step of periodically providing more aqueous, isotonic, substantially cell-free solution through a priming solution tube connected to a source of priming solution and connecting in branching relation with said branch connection tube, to flush said aqueous solution in said branch connection tubing which has become mixed with blood into the blood flow tubing.

14. The method of claim 13 in which an interface between said blood and aqueous solution moves longitudinally in said tubing of no more 5 mm. diameter as said pressure varies.

15. The method of claim 13 in which said branch connection tubing defines an in-line, enlarged chamber that extends for no more than 10 percent of the length of said branch connection tubing.

16. The method of claim 1 in which the majority of said branch connection tubing has an inner diameter of substantially no more than 5 mm.

17. The method of sensing pressure in blood flow tubing, which comprises:

placing an aqueous, physiological, substantially cell-free solution into branch connection tubing that connects in branching relation with said blood flow tubing at one end;

maintaining a sealed air volume occupying a portion of said branch connection tubing spaced from said blood flow tubing by said solution; and flowing positively or negatively pressurized blood through said blood flow tubing, whereby the pressure of said blood is communicated through said aqueous solution to the air volume for indication of the pressure in said blood.

18. The method of claim 17 in which said air volume transmits pressure to a pressure indicator.

19. The method of claim 18 in which said pressure indicator is an electronic pressure transducer.

20. The method of claim 19 in which said branch connection tubing has an inner diameter of substantially no more than 5 mm. along most of its length, said branch connection tubing also defining an in-line, enlarged chamber.

21. The method of claim 17 in which said branch connection tubing has an inner diameter of substantially no more than 5 mm. along most of its length, said branch connection tubing also defining an in-line, enlarged chamber.

\* \* \* \* \*